United States Patent
Sauer et al.

(10) Patent No.: US 6,685,630 B2
(45) Date of Patent: *Feb. 3, 2004

(54) OPTICAL TROCAR

(75) Inventors: Jude S. Sauer, Pittsford, NY (US); Michael G. Oravecz, Rochester, NY (US); Roger J. Greenwald, Holly, NY (US); Alexander I. Kobilansky, Pittsford, NY (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/116,796

(22) Filed: Apr. 5, 2002

(65) Prior Publication Data

US 2002/0143236 A1 Oct. 3, 2002

Related U.S. Application Data

(63) Continuation of application No. 09/494,101, filed on Jan. 28, 2000, now abandoned, which is a continuation of application No. 08/869,880, filed on Jun. 5, 1997, now abandoned, which is a continuation of application No. 08/710,282, filed on Sep. 13, 1996, now abandoned, which is a continuation of application No. 08/407,929, filed on Mar. 21, 1995, now Pat. No. 5,569,160, which is a continuation of application No. 08/132,403, filed on Oct. 6, 1993, now Pat. No. 5,467,762, which is a continuation-in-part of application No. 08/120,489, filed on Sep. 13, 1993, now Pat. No. 5,441,041.

(51) Int. Cl.[7] .................................................. A61B 1/00

(52) U.S. Cl. ........................ 600/114; 600/104; 600/106; 606/185

(58) Field of Search ................................ 600/104, 105, 600/106, 114, 121, 129, 175, 160; 604/164.01, 164.06, 164.12; 606/185

(56) References Cited

U.S. PATENT DOCUMENTS

| | | | |
|---|---|---|---|
| 1,380,447 A | 6/1921 | Wescott |
| 1,727,495 A | 9/1929 | Wappler |
| 2,699,770 A | 1/1955 | Fourestier et al. |
| 2,764,148 A | 9/1956 | Sheldon |
| 2,764,149 A | 9/1956 | Sheldon |
| 2,877,368 A | 3/1959 | Sheldon |
| 3,021,834 A | 2/1962 | Sheldon |
| 3,417,745 A | 12/1968 | Sheldon |
| 3,437,747 A | 4/1969 | Sheldon |
| 3,499,107 A | 3/1970 | Sheldon |
| 3,538,916 A | 11/1970 | Wiles |
| 3,556,085 A | 1/1971 | Takahashi |
| 3,762,416 A | 10/1973 | Moss et al. |

(List continued on next page.)

FOREIGN PATENT DOCUMENTS

| | | |
|---|---|---|
| DE | 1616107 | 4/1971 |
| DE | 2538758 | 3/1977 |
| DE | 2800607 | 10/1978 |

(List continued on next page.)

OTHER PUBLICATIONS

US 4,961,414, 10/1990, Cho et al. (withdrawn)

Primary Examiner—John P. Leubecker

(57) ABSTRACT

The present invention relates to an optical obturator which includes a sleeve having a longitudinal bore between a proximal end and a distal end. The longitudinal bore of the sleeve is configured to receive at least a portion of an endoscope or like image transferring system. An image passing member, such as an optical window is positioned at the distal end of the sleeve and is provided to permit optical images to pass into the longitudinal bore of the sleeve and to permit illumination light to pass to the surgical site. An automatically retracting blade is positioned distal to the image passing member to facilitate penetration of body tissue.

19 Claims, 7 Drawing Sheets

U.S. PATENT DOCUMENTS

| | | | |
|---|---|---|---|
| 3,809,095 A | | 5/1974 | Cimber |
| 3,915,169 A | | 10/1975 | McGuire |
| 3,961,621 A | | 6/1976 | Northeved |
| 4,137,920 A | * | 2/1979 | Bonnet ............... 606/171 |
| 4,210,146 A | | 7/1980 | Banko |
| 4,220,155 A | | 9/1980 | Kimberling et al. |
| 4,254,762 A | | 3/1981 | Yoon |
| 4,256,119 A | | 3/1981 | Gauthier |
| 4,269,192 A | | 5/1981 | Matsuo |
| 4,345,589 A | | 8/1982 | Hiltebrandt |
| 4,411,653 A | | 10/1983 | Razi |
| 4,461,305 A | | 7/1984 | Cibley |
| 4,516,575 A | | 5/1985 | Gerhard et al. |
| 4,535,773 A | | 8/1985 | Yoon |
| 4,539,976 A | | 9/1985 | Sharpe |
| 4,559,041 A | | 12/1985 | Razi |
| 4,566,438 A | | 1/1986 | Liese et al. |
| 4,570,632 A | | 2/1986 | Woods |
| 4,653,475 A | | 3/1987 | Seike et al. |
| 4,667,684 A | | 5/1987 | Leigh |
| 4,723,545 A | | 2/1988 | Nixon |
| 4,733,671 A | | 3/1988 | Mehl |
| 4,790,312 A | | 12/1988 | Capuano, Sr. et al. |
| 4,865,029 A | | 9/1989 | Pankratov et al. |
| 4,904,246 A | | 2/1990 | Atkinson |
| 4,957,112 A | | 9/1990 | Yokoi et al. |
| 4,962,770 A | | 10/1990 | Agee et al. |
| 4,976,269 A | | 12/1990 | Mehl |
| 4,991,600 A | | 2/1991 | Taylor |
| 5,066,288 A | | 11/1991 | Deneiga et al. |
| 5,089,000 A | | 2/1992 | Agee et al. |
| 5,092,872 A | | 3/1992 | Segalowitz |
| 5,104,382 A | | 4/1992 | Brinkerhoff et al. |
| 5,116,353 A | | 5/1992 | Green |
| 5,146,921 A | | 9/1992 | Terwilliger et al. |
| 5,152,754 A | | 10/1992 | Plyley et al. |
| 5,158,552 A | | 10/1992 | Borgia et al. |
| 5,159,920 A | | 11/1992 | Condon et al. |
| 5,176,695 A | | 1/1993 | Dulebohn |
| 5,183,053 A | | 2/1993 | Yeh et al. |
| 5,186,178 A | | 2/1993 | Yeh et al. |
| 5,250,068 A | | 10/1993 | Ideguchi et al. |
| 5,271,380 A | | 12/1993 | Riek et al. |
| 5,275,583 A | | 1/1994 | Crainich |
| 5,290,276 A | * | 3/1994 | Sewell, Jr. ............... 606/15 |
| 5,314,417 A | | 5/1994 | Stephens et al. |
| 5,334,150 A | * | 8/1994 | Kaali ............... 604/164.08 |
| 5,354,302 A | | 10/1994 | Ko |
| 5,372,588 A | | 12/1994 | Farley et al. |
| 5,385,572 A | * | 1/1995 | Nobles et al. ............... 606/185 |
| 5,406,940 A | | 4/1995 | Melzer et al. |
| 5,431,151 A | * | 7/1995 | Riek et al. ............... 600/104 |
| 5,467,762 A | * | 11/1995 | Sauer et al. ............... 600/114 |

FOREIGN PATENT DOCUMENTS

| | | |
|---|---|---|
| DE | 2922239 | 3/1982 |
| DE | 9112976 | 12/1991 |
| DE | 4133073 | 4/1992 |
| DE | 4035146 | 5/1992 |
| EP | 135364 | 3/1985 |
| EP | 0433581 | 6/1991 |
| EP | 0484725 | 5/1992 |
| EP | 0604197 | 6/1994 |
| GB | 719538 | 12/1954 |
| GB | 1215383 | 12/1970 |
| GB | 2048686 | 12/1980 |
| SU | 537677 | 12/1976 |
| SU | 942730 | 7/1982 |
| WO | 9214514 | 9/1992 |

* cited by examiner

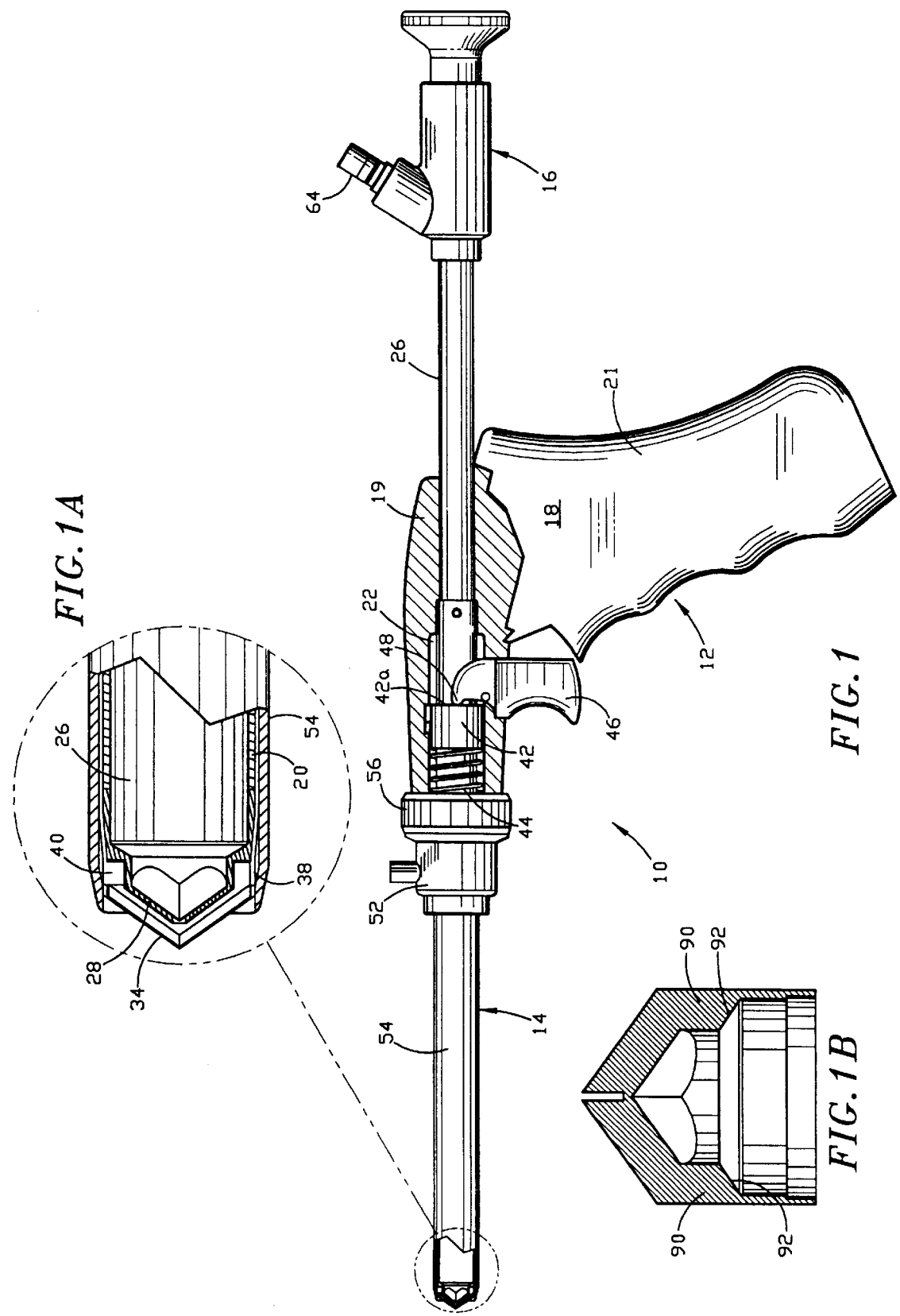

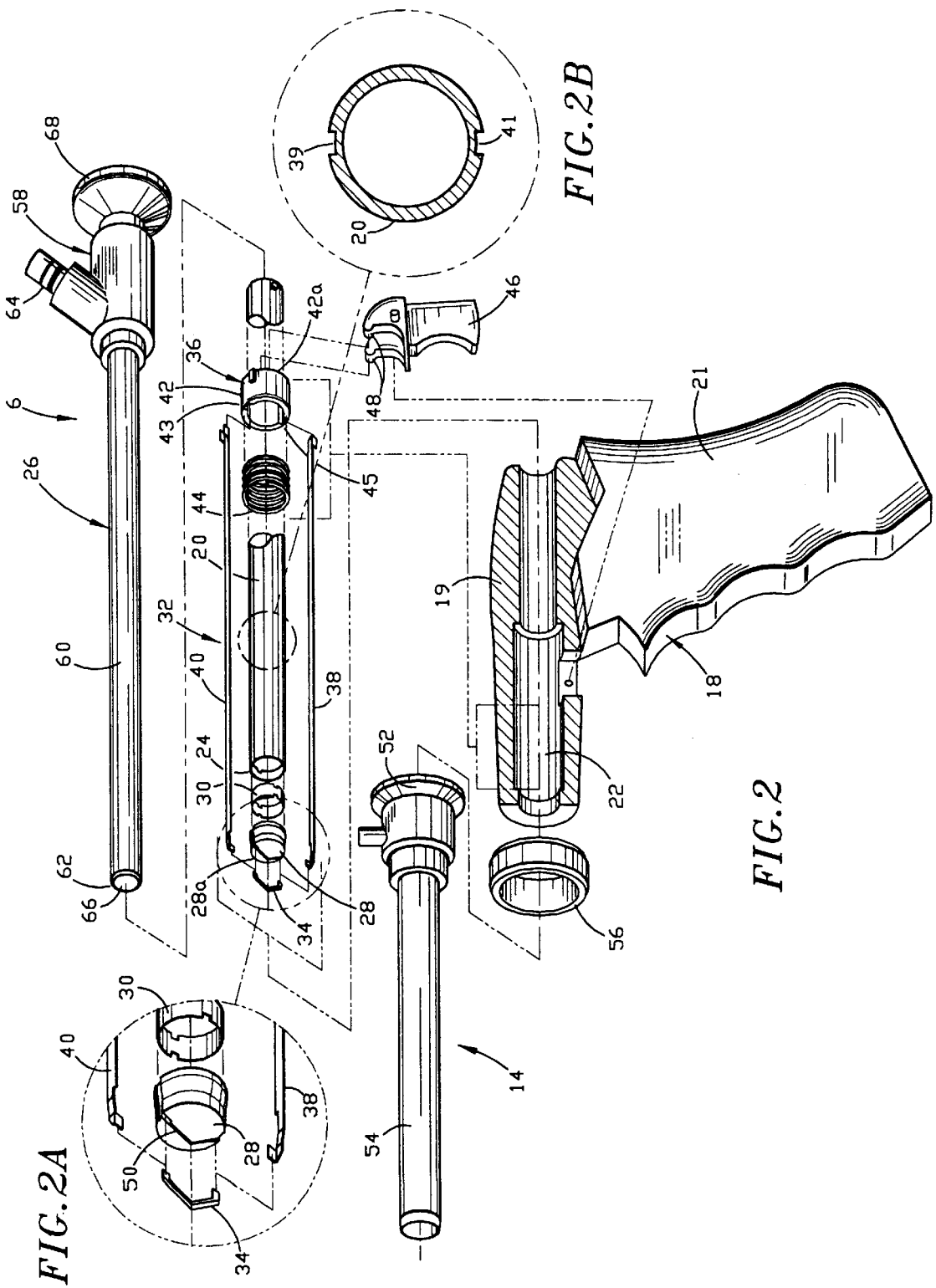

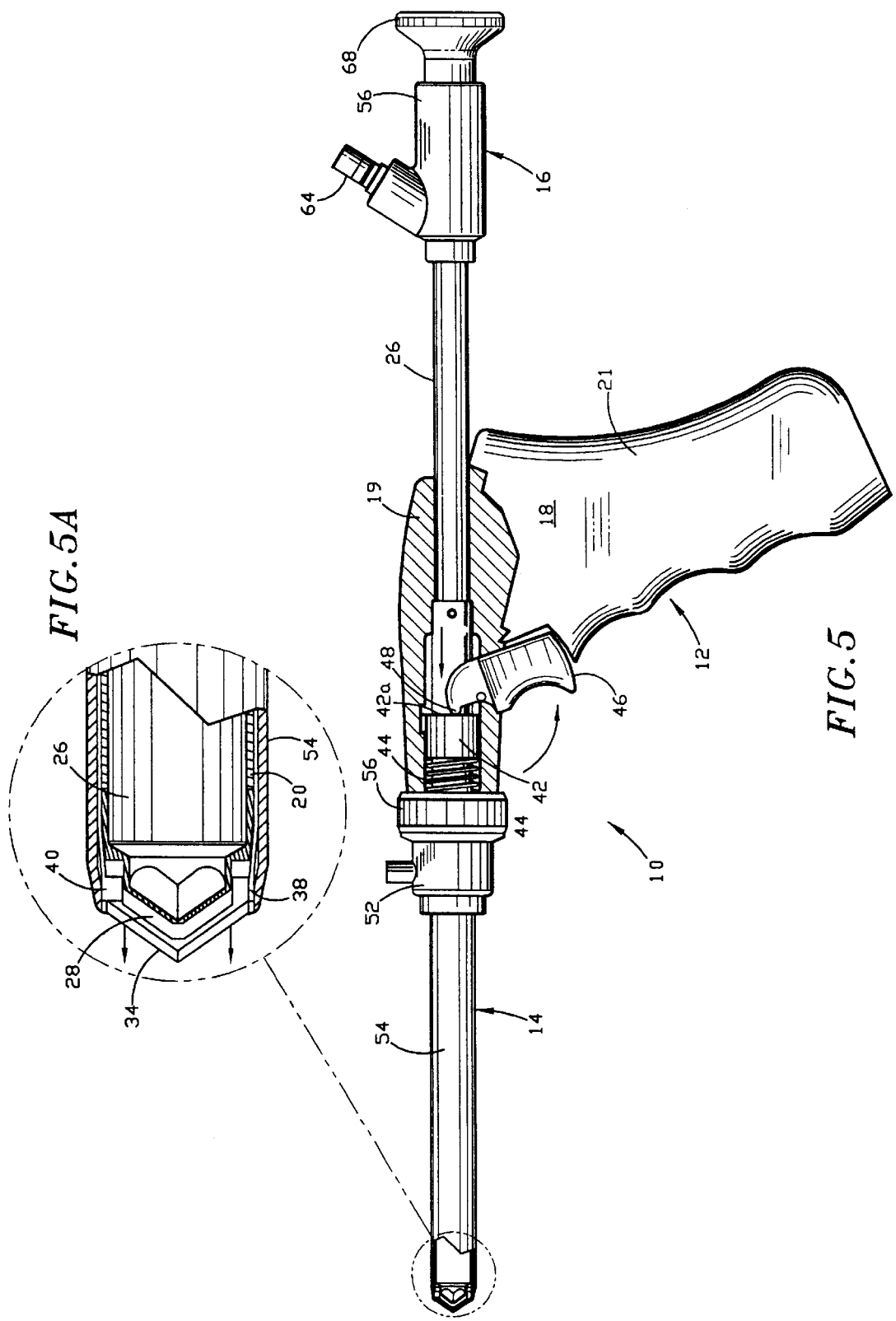

OPTICAL TROCAR

CROSS-REFERENCE TO RELATED APPLICATIONS

This application is a continuation of co-pending U.S. application Ser. No. 09/494,101, filed Jan. 28, 2000, now abandoned, which is a continuation of U.S. application Ser. No. 08/869,880, filed Jun. 5, 1997, now abandoned, which is a continuation of U.S. application Ser. No. 08/710,282, filed Sep. 13, 1996, now abandoned, which is a continuation of U.S. application Ser. No. 08/407,929, filed Mar. 21, 1995, now U.S. Pat. No. 5,569,160, which is a continuation of U.S. application Ser,. No. 08/132,403, filed Oct. 6, 1993, now U.S. Pat. No. 5,467,762, which is a continuation-in-part of U.S. application Ser. No. 08/120,489, filed Sep. 13, 1993, now U.S. Pat. No. 5,441,041, all of which are incorporated herein by reference in their entirety.

BACKGROUND OF THE INVENTION

1. Field of the Invention

The present invention relates to an apparatus for penetrating and for observing penetration of body tissue. More particularly, the present invention relates to a trocar assembly having an endoscope or laparoscope inserted therethrough to provide visual observation during penetration of the peritoneum or other body tissue.

2. Description of the Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through a small incision or through narrow endoscopic tubes (cannulas) inserted through small entrance wounds in the skin. In laparoscopic procedures surgery is performed in the interior of the abdomen.

Laparoscopic procedures generally utilize instrumentation that is internally sealed to inhibit gases from entering or exiting the body through the laparoscopic or endoscopic incision. This is particularly true in surgical procedures in which the surgical region is insufflated. Moreover, laparoscopic and endoscopic procedures often require the surgeon to act on organs, tissues and vessels far removed from the incision, thereby requiring that any instruments to be used in such procedures be of sufficient size and length to permit remote operation. Typically, after the surgical region is insufflated, trocars are used to puncture the body cavity and include a cannula which remains in place for use during endoscopic procedures. Generally, trocars used during such procedures include a stylet having a sharp tip for penetrating the body cavity positioned coaxially within protective tubes to protect a patient or surgeon from inadvertent contact with the tip. An example of a known trocar is described in commonly assigned, U.S. Pat. No. 4,601,710 to Moll. Most currently used trocars rely on protective tubes or relative retraction of the tip to prevent inadvertent contact with tissue.

The present invention provides a trocar assembly for observing the penetration of the peritoneum or other body portions. The trocar assembly of the present invention provides an improved window structure for passing optical images to an imaging system inserted into or formed within the trocar assembly, which provides a clear and bright image of the body tissue being penetrated. The assembly also includes a light pipe for passing illumination light to body tissue. In addition, the present invention provides an improved cutting tip for penetration of body tissue.

SUMMARY OF THE INVENTION

The present invention relates to a trocar which includes a cannula assembly, an obturator assembly and an image passing system. The cannula assembly includes a cannula housing and a cannula sleeve extending from said cannula housing. The obturator assembly includes an obturator sleeve having a proximal end, a distal end and a longitudinal bore therebetween which are configured for coaxial alignment with the cannula assembly.

An image passing member is positioned at the distal end of the obturator sleeve and is provided to permit passage of optical images into the longitudinal bore of the sleeve and permit passage of illumination light to body tissue. A tissue penetrating member, such as a blade, is positioned adjacent the distal end of the obturator sleeve and distal to the image passing member and is preferably movable between non-deployed and deployed positions. The tissue penetrating member is configured to facilitate observation of body tissue simultaneous with penetration of body tissue.

In the preferred embodiment, the image passing member is an optical with substantially flat surfaces for receiving optical images. Alternatively, the optical window includes at least one conical surface for receiving the optical images.

Image transferring means, such as an endoscope, is preferably removably positioned within the longitudinal bore of the obturator sleeve and is provided to transmit illumination light through the image passing member to the surgical site and to transmit optical images from the image passing member to a proximal end of the obturator housing for subsequent viewing by the surgeon.

The tissue penetrating blade is operatively associated with an actuating member positioned within the obturator housing. Preferably, the actuating member is configured to move the blade to a deployed position and to automatically move the blade to a non-deployed position after the blade has been deployed.

In the preferred embodiment, the actuating member includes a blade drive member slidably positioned within the obturator housing and operatively connected to the blade, and a trigger member which is pivotally connected to the obturator housing. An automatic release member is operatively associated with the trigger member and the blade drive member so that when the blade is moved to the deployed position, the release member actuates to facilitate movement of the blade to the non-deployed position.

BRIEF DESCRIPTION OF THE DRAWINGS

The preferred embodiments of the invention are described hereinbelow with reference to the drawings wherein:

FIG. 1 is a side elevational view in partial cross-section of the apparatus according to the present invention, illustrating an endoscope positioned within a trocar assembly having a movable cutting blade;

FIG. 1A is an enlarged partial cross-sectional view of the distal end of the apparatus of FIG. 1, illustrating the cutting blade in a non-deployed position;

FIG. 1B is an enlarged view of an alternate embodiment of the image passing member;

FIG. 2 is an exploded perspective view of the instrument of FIG. 1 with parts separated, illustrating an actuating assembly for moving the cutting blade;

FIG. 2A is an exploded perspective view of an image passing member and blade according to the present invention;

FIG. 2B is a cross-sectional view of the obturator sleeve of the present invention;

FIG. 5 is a side elevational view similar to FIG. 1, illustrating actuation of the trigger assembly to move the blade to a deployed position;

FIG. 5A is an enlarged partial cross-sectional view of the distal end of the apparatus of FIG. 5, illustrating the cutting blade in the deployed position;

DETAILED DESCRIPTION OF THE PREFERRED EMBODIMENTS

Figure 4:
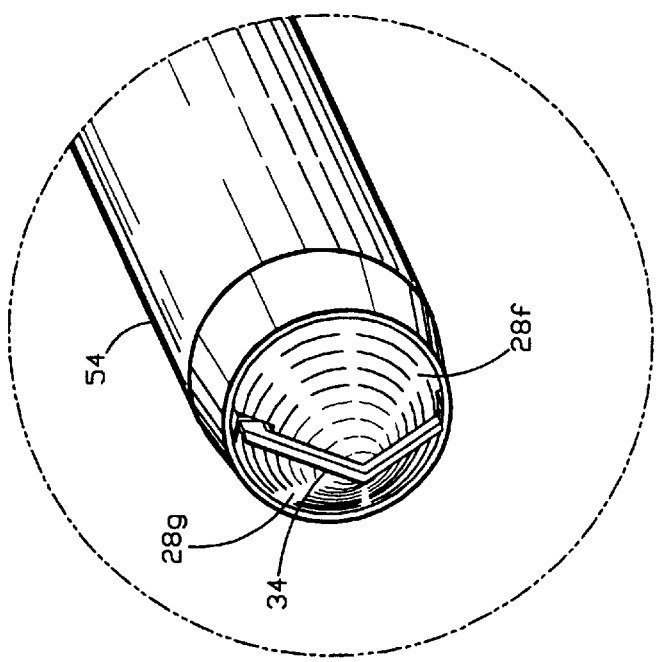
FIGS. 3 and 4 illustrate alternative embodiments for the configuration of the distal end portion of the trocar assembly according to the present invention.

The apparatus of the present invention is provided to penetrate body tissue, e.g., the abdominal wall, and to provide a simultaneous forward directional view of the body tissue being penetrated. In the preferred embodiment, the apparatus includes a trocar assembly 10 having an obturator assembly 12 and a cannula assembly 14, and an endoscope 16 which is positioned within the obturator assembly to provide observation of the body tissue being penetrated. The term obturator assembly as used herein refers to the tissue penetrating assembly of the trocar assembly.

Referring to FIGS. 1 and 2, obturator assembly 12 includes housing 18 and a longitudinally extending obturator sleeve 20. Preferably, obturator housing 18 includes barrel portion 19 and hand grip 21. The proximal end of obturator sleeve 20 is secured within channel 22 of barrel portion 19 so that the obturator sleeve 20 extends outwardly from the obturator housing 18. Hand grip 21 is provided for manual gripping to facilitate penetration of the body tissue. Obturator sleeve 20 has a longitudinal bore 24 which extends between the proximal end and distal end. The longitudinal bore 24 is configured and dimensioned to receive the endoscopic portion 26 of the endoscope 16, as shown in FIG. 1.

Figure 3:
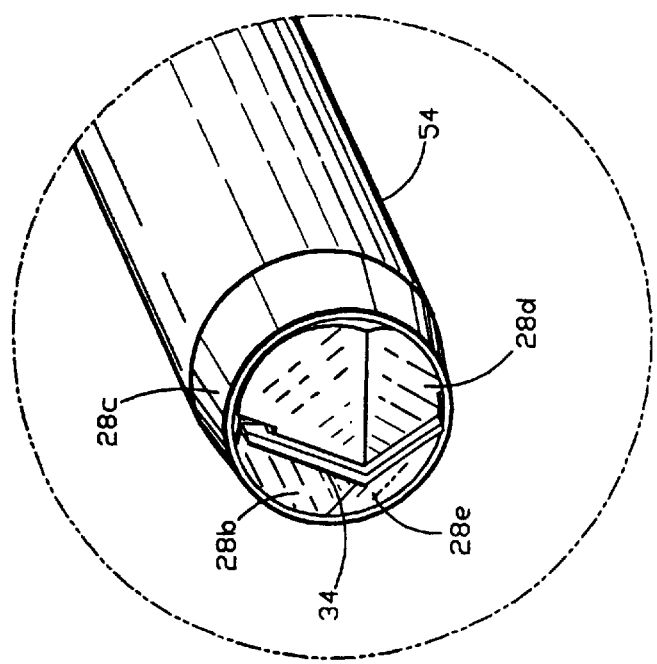

Referring to FIGS. 2, 3 and 4, an image passing member 28 is secured to the distal end of obturator sleeve 20 via retaining ring 30. In one embodiment, the image passing member is a transparent optical window fabricated from a variety of materials such as polystyrene, polymethylmethacrylate (PMMA), polyurethane, transparent epoxies and/or glass or other transparent materials. (When made of plastic material, the cost is reduced.) The window, as shown in FIG. 3, includes a set of four substantially flat surfaces 28a, 28b, 28c and 28d. In this embodiment the flat surfaces of the optical window permit passage of the optical image into the longitudinal bore of the obturator sleeve so as to provide a clear image. The image passing member may alternately include a set of two conical surfaces 28f and 28g, shown in FIG. 4, which pass an optical image into the longitudinal bore 24 of obturator sleeve 20.

In another embodiment, the image passing member is an image directing member. In this configuration, optical images which impinge the distal end 28a of image directing member 28 are directed into longitudinal bore 24 of obturator sleeve 20. The image directing member may be a lens, an optical prism, an optical mirror, or like image directing medium and is preferably configured to allow close to a 360° forward angle of view. In the preferred embodiment, image directing member 28 is a prism which includes a set of four substantially flat surfaces 28a, 28b, 28c, and 28d as shown in FIG. 3. The corresponding inner surfaces are also preferably substantially flat. The flat surfaces direct the optical image into the longitudinal bore of the obturator sleeve so as to provide a clear image. Alternatively, the image directing member is a lens which includes a set of two conical surfaces 28f and 28g which direct an optical image into the longitudinal bore 24 of obturator sleeve 20 (see FIG. 4).

The image passing member also allows for passage of illumination light from the obturator sleeve 20 to body tissue. As shown in FIG. 1B, the passage member can be in the form of light pipe 90 having an angled surfaces 92. Alternatively, the surfaces can be straight or angled other than that shown to achieve the purpose of allowing illumination light to pass therethrough. The image passing member, e.g. the window, and the light pipe can have spherical or conical surfaces and can be integral as shown. Alternatively, they can be formed as two separate parts, i.e. one channel for illumination and another for imaging. In a preferred embodiment, the light pipe 90 is cylindrical in configuration to accommodate the annular array of fiber optic elements of the endoscope described below.

The image passing member 28 is shown having a convex outer surface, however, other configurations can be utilized.

Referring again to FIG. 2, the cutting portion 32 of obturator assembly 12 includes a cutting blade 34 connected to actuating assembly 36. Actuating assembly 36 is provided to move blade 34 between a non-deployed position (FIG. 1A) and a deployed position (FIG. 5A) which will be described in more detail below. The cutting blade 34 is preferably centered with respect to the outer surface of the image passing member as shown. Thus, in visualization, the cutting blade is seen as a thin line through the center, i.e. bisecting, the viewing field so as not to obstruct viewing of the body.

Actuating assembly 36 includes blade pusher arms 38 and 40, blade drive member 42, drive spring 44 and trigger 46. Blade 34 can be formed as an integral piece with blade drive member 42 and/or blade arms 38, 40. Alternately blade 34 can be connected such as by welding, to the distal end of blade pusher arms 38 and 40 which extend along the longitudinal axis of obturator sleeve 20 within slots 39 and 41 in obturator sleeve 20, shown in FIG. 2B. The proximal end of blade pusher arms 38 and 40 are secured within slots 43 and 45 of blade drive member 42, as shown. Blade drive member 42 and drive spring 44 are positioned within channel 22 of obturator housing 18 so that drive spring 44 normally biases blade drive member 42 toward the proximal end of obturator housing 18, thus biasing blade 34 to the proximal non-deployed position.

Trigger 46 is pivotally secured to obturator housing 18 via pin 47, as shown, so that camming surface 48 of trigger 46 engages the proximal end portion 42a of blade drive member 42. Thus, actuation of trigger 46, i.e. movement in the direction of the arrow in FIG. 5, causes camming surface 48 to engage blade drive member 42 and move the drive member distally within channel 22. Distal movement of drive member 42 causes blade pusher arms 38 and 40 to move distally to move blade 34 distally to the deployed (extended) position. Release of trigger 46 permits blade 34 to return to the non-deployed position in response to the action of drive spring 44 forcing blade drive member 42 proximally.

The movement of blade 34 between non-deployed and deployed positions can be seen by comparing FIGS. 1 and 5. As shown in FIGS. 1 and 1A, in the non-deployed position the blade 34 is at rest within recess 50 (FIG. 2A) in image directing member 28. In the deployed position blade 34 is extended from recess 50 beyond the distal end of cannula assembly 14, as shown in FIG. 5.

Figure 6:
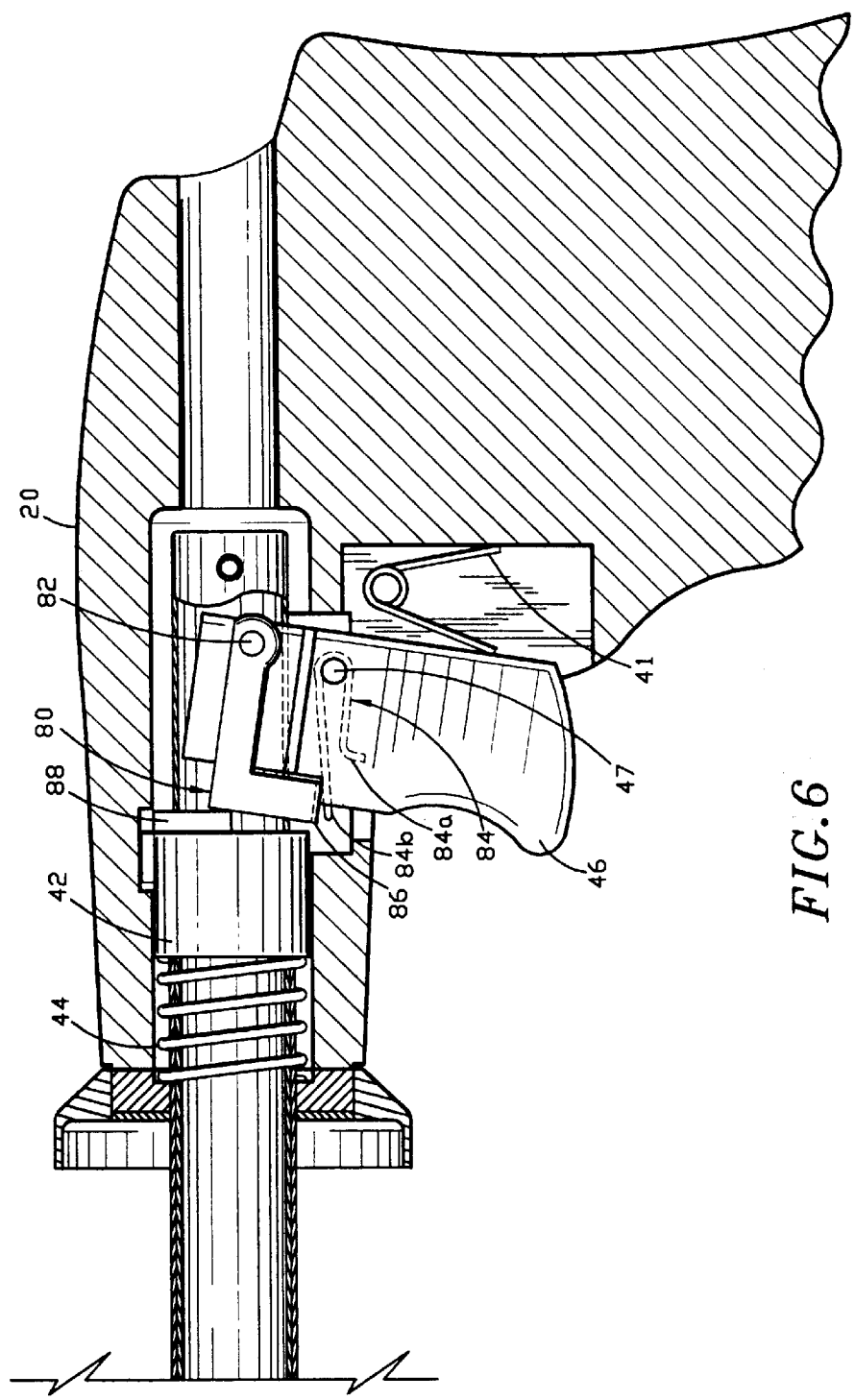
FIGS. 6–8 are side elevational views of an alternative embodiment of the blade actuation mechanism of the present invention.
Figure 7:
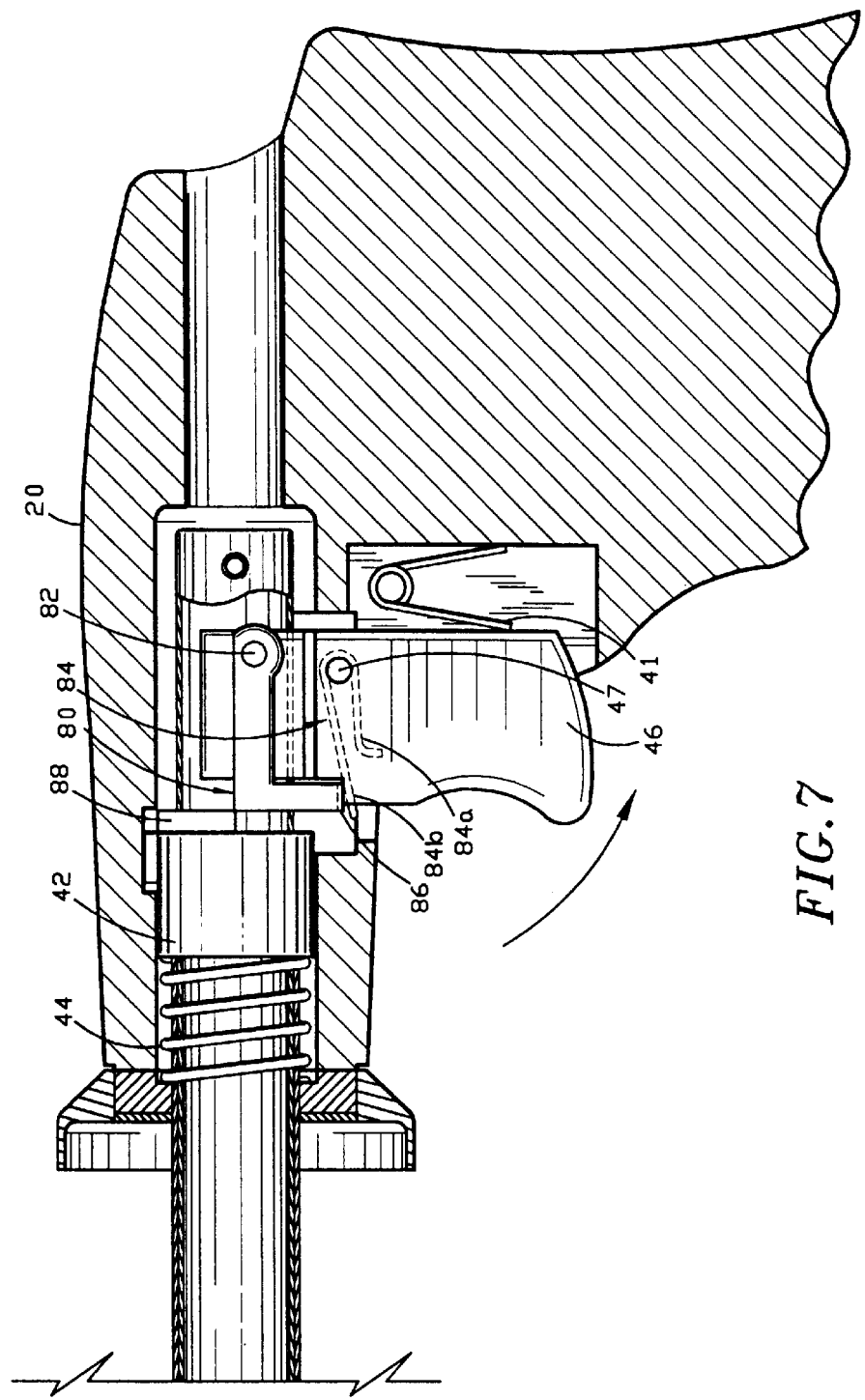
Figures 8, 8A:
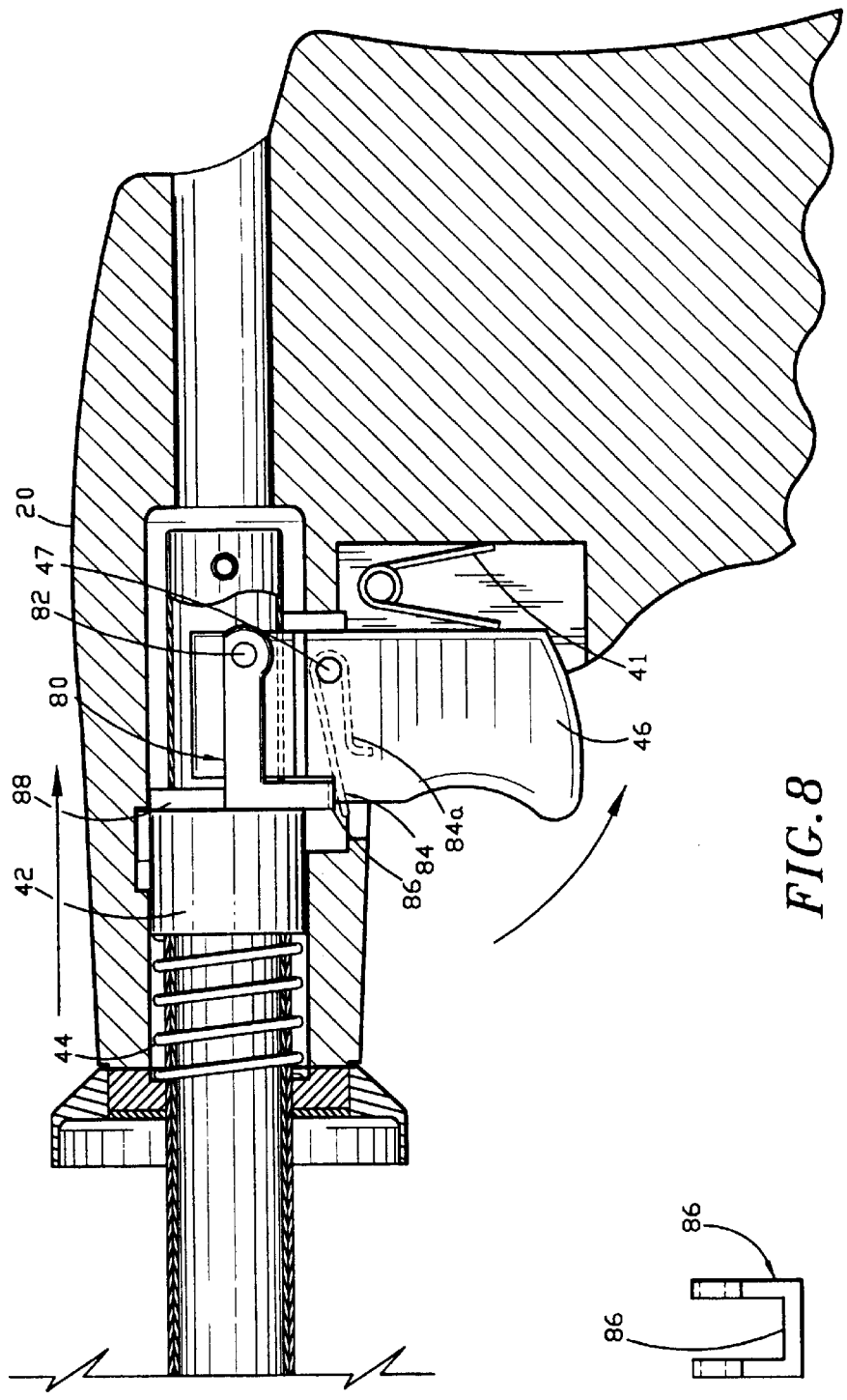
FIG. 8A is a rear plan view of a portion of the automatic release member of the present invention.

In an alternative embodiment shown in FIGS. 6–8, an automatic release member is associated with blade drive member 42 and trigger 46 and is provided to automatically return blade 34 to the non-deployed position after the blade is deployed. That is, the blade 34 returns to its initial undeployed position without requiring release of the trigger 46.

Trigger 46 is pivotally secured to obturator housing 18 via pin 47 and lever 80 is pivotally secured to trigger 46 via lever pin 82. Spring 41 biases trigger 46 distally. Lever spring 84 is secured to trigger 46 at one end 84a and is positioned around pin 47, as shown. The biasing arm 84b of lever spring 84 engages crossbar 86 of lever 80 and is provided to pivot lever 80 clockwise a predetermined angular distance, such as 12°. Lever bushing 88 is secured to the upper portion of blade drive member 42, as shown, and is provided to engage lever 80. When trigger 46 is in the armed position, i.e., trigger 46 is ready for actuation, lever 80 is biased upward by lever spring 84 so that the upper portion of lever 80 engages lever bushing 88, as shown in FIG. 6.

Referring to FIG. 7, actuation of trigger 46, i.e., movement of the trigger in the proximal direction, causes lever 80 to move blade drive member 42 distally to compress drive spring 44 and to advance blade 34 to the deployed position, shown in FIG. 5A. Lever 80 pivots counter-clockwise with the actuation of trigger 46.

Referring now to FIG. 8, further movement or actuation of trigger 46 in the proximal direction causes lever 80 to continue to pivot counter-clockwise so that the portion of lever 80 engaging lever bushing 88 disengages therefrom. As a result, blade drive member 42 moves proximally under the action of drive spring 44 to move blade 34 to the non-deployed position, shown in FIG. 1. Once the blade is in the non-deployed position, the image passing member 28 prohibits further proximal movement of blade drive member 42 as described above. Lever 80 also prevents such proximal movement. To re-arm lever 80, trigger 46 is released. Trigger 46 is consequently forced clockwise by spring 41 causing lever 80 to pivot clockwise past bushing 88 as it is pulled slightly proximally by such clockwise movement of trigger 46. When trigger 46 returns to the original, i.e. actuation, position of FIG. 6, lever spring 84 biases lever 80 clockwise to a position which permits engagement with lever bushing 88.

Referring again to FIG. 2, cannula assembly 14 includes cannula housing 52 and cannula sleeve 54 secured to the cannula housing 52 and extending outwardly therefrom. obturator housing 18 incldues bushing 56 which is configured and dimensioned to interfit with the proximal end of cannula housing 52, as shown in FIG. 1, so that obturator sleeve 20 coaxially aligns with cannula sleeve 54 when the two assemblies are interfitted. The cannula sleeve 54 is adapted to remain in the body after penetration and subsequent removal of the obturator assembly 12 (and endoscope 10) to allow insertion of appropriate endoscopic/laparoscopic instrumentation therethrough.

To maintain a gas tight seal within the cannula housing, a sealing member or system may be positioned therewithin which is adapted to receive the obturator assembly 12 of the present invention as well as other endoscopic surgical instruments. One example of a suitable sealing system utilizes a duckbill sealing member. A more detailed description of an exemplary cannula assembly and sealing system is found in U.S. Pat. No. 5,180,373 issued Jan. 19, 1993, which is incorporated herein by reference.

Referring to FIGS. 1A and 2, endoscope 16 includes endoscopic portion 26 and endoscope housing 58. Endoscopic portion 26 is configured to transfer illuminating light from endoscope housing 58 to the distal end of the endoscopic portion to provide illuminating light to the operative site. In an exemplary configuration, endoscopic portion 26 includes an outer sheath 60 and an annular array of fiber optic elements 62 extending between light source connector 64 of endoscope housing 58 and the distal end of outer sheath 60 to illuminate the operative site. Any known light source may be connected to connector 64 to provide the illuminating light. In addition, endoscopic portion 26 includes an image transferring system 66 which may include CCD's, a bundle of fiber optic elements or objective lenses which transfer an optical image to eyepiece 68 for viewing. Alternatively, a video system including a monitor may be operatively connected to housing 58 to provide a video image of the body tissue being penetrated. Preferably, the fiber optic elements 62 are positioned adjacent the inner wall of the outer sheath so as to surround the image transferring system. In this configuration, illumination light from the endoscope is passed through the light pipe portion of image passing member and optical images which impinge on the image passing member 28 pass into the image transferring system and relayed to eyepiece 68. An example of an endoscope which can be utilized is described in U.S. Pat. No. 4,964,710 incorporated herein be reference.

In operation, endoscope 16 is inserted into the trocar assembly 10, i.e. into longitudinal bore 24 of obturator sleeve 20, as shown in FIG. 1. The surgeon then positions the blade 34 against the body tissue and may continuously move blade 34 between the non-deployed and deployed positions, i.e., reciprocally moving blade 34, via actuating assembly 32. Pressure is applied to hand grip 21 in the distal direction to penetrate the body tissue. The movement of blade 34 facilitates cutting of the body tissue, thus permitting the surgeon to apply relatively minimal pressure to hand grip 21 to penetrate the body tissue.

During penetration of the body tissue the surgeon either observes such penetration through eyepiece 68, or in instances where a video system is utilized the surgeon simply observes the penetration of the body tissue via any known video monitor.

Once the surgeon penetrates the body tissue as observed through endoscope 16, the surgeon releases trigger 46 to permit blade 34 to return to the non-deployed position and discontinues application of pressure to hand grip 21. According to the above-described alternative embodiment for the trigger arrangement, once the trigger 46 is fully actuated, blade 34 automatically returns to the non-deployed position and release of trigger 46 re-arms the automatic release member.

In operation, the surgeon may also more selectively deploy the blade 34 during penetration. That is, the surgeon may insert the trocar assembly and bluntly penetrate the body tissue until reaching thicker tissue, such as muscle. At this point, the blade can be deployed to penetrate (cut through) this thick tissue, then retracted to provide blunt penetration until thick tissue is again encountered where once again the blade can be deployed.

After penetration into the body cavity, both the endoscope 16 and the obturator assembly 12 are removed from the cannula assembly 14, leaving the cannula assembly 14 in the body for insertion of desired instrumentation therethrough.

In an alternate embodiment, the obturator assembly 12 and endoscope 16 or optical components thereof can be a single unit inserted into cannula assembly 14. For example, the obturator assembly can be manufactured with illumination optics and/or imaging optics positioned therein so that the obturator assembly itself can function to penetrate tissue as well as to light the surgical site and transmit images to the video monitor. In this version, the obturator would not have a longitudinal bore and it would be sealed.

Additionally, in an alternate embodiment of the penetrating blade member, the blade member can be fixedly attached to the obturator assembly so that it remains in an exposed position. The blade or cutting member can also alternatively be movable in directions other than longitudinally as described above, such as transverse to the longitudinal axis, or the blade can vibrate.

It will be understood that various modifications can be made to the embodiments of the present invention herein disclosed without departing from the spirit and scope thereof. For example, various diameters for the cannula assembly, the obturator assembly, as well as various diameter endoscopes are contemplated. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. A trocar which comprises:
   a cannula;
   an obturator configured for insertion into said cannula, said obturator having a proximal end, a distal end and a longitudinal bore;
   an image passing member positioned on said distal end of said obturator for allowing optical images to pass into said longitudinal bore; and
   means for penetrating body tissue positioned at said distal end of said obturator, said penetrating means being movable in relation to said image passing member between a non-deployed position and a deployed position.

2. The trocar according to claim 1, wherein said image passing member is an optical window having four substantially flat surfaces for receiving optical images.

3. The trocar according to claim 1, wherein said image passing member is an optical window having at least one substantially conical surface for receiving optical images.

4. The trocar according to claim 1, wherein said means for penetrating body tissue comprises a blade operatively connected to an actuating member such that actuation of said actuating member moves said blade to said deployed position.

5. The trocar according to claim 1, wherein said penetrating means includes a blade, and further comprising an actuating member for moving said blade, wherein initial movement of said actuating member in a first direction moves said blade to said deployed position and further movement of said actuating member in said first direction moves said blade to said non-deployed position.

6. The trocar according to claim 5, further comprising a blade drive member slidably positioned within said obturator and operatively connected to said blade.

7. The trocar according to claim 1, wherein said image passing member is configured to allow passage of illumination light to the body tissue.

8. The trocar according to claim 1, further comprising a light pipe positioned adjacent said distal end of said obturator to allow passage of illumination light to body tissue.

9. The trocar according to claim 8, wherein said image passing member and said light pipe are integral.

10. Apparatus for observation of body tissue during penetration which comprises:
    a cannula assembly having a cannula housing and a cannula sleeve extending from said cannula housing, said cannula sleeve having a longitudinal bore extending from a proximal end to a distal end;
    an obturator assembly having an obturator housing and an obturator sleeve, said obturator sleeve being configured for coaxial alignment with said cannula sleeve, a distal end of said obturator sleeve having an image passing member positioned thereon, the image passing member having a recess, and the obturator assembly further having means for penetrating body tissue positioned at least partially within the recess of said image passing member.

11. The apparatus according to claim 10, wherein said receiving means comprises a longitudinal bore formed in said obturator sleeve.

12. The apparatus according to claim 11, wherein said image passing member comprises an optical window having four substantially planar surfaces for passing optical images into said bore of said obturator sleeve.

13. The apparatus according to claim 11, wherein said image passing member comprises an optical window having at least one substantially conical surface for passing optical images into said bore of said obturator sleeve.

14. The apparatus according to claim 11, wherein said means for penetrating body tissue comprises a blade configured to permit optical images to impinge said image passing member from a substantially 360 degree forward angle of view.

15. The apparatus according to claim 14, wherein said blade is operatively associated with an actuating member positioned within said obturator housing, said actuating member being configured to move said blade to a deployed position and to automatically move said blade to a non-deployed position after said blade has been deployed.

16. The apparatus according to claim 15, wherein said actuating member comprises:
    a blade drive member slidably positioned within said obturator housing and operatively connected to said blade such that said blade is movable between deployed and non-deployed positions; and
    a trigger member pivotally connected to said obturator housing and having an automatic release member operatively associated with said trigger member and said blade drive member such that when said blade is moved to said deployed position said automatic release member actuates to facilitate movement of said blade to said non-deployed position.

17. The apparatus according to claim 16, wherein said automatic release member comprises a lever pivotally connected to said trigger member and a bushing connected to said blade drive member such that said lever engages said bushing to deploy said blade in response to pivotal movement of said trigger member and such that said lever disengages from said bushing when said trigger member is actuated to a predetermined position so as to facilitate movement of said blade to said non-deployed position.

18. The apparatus according to claim 10, wherein said image passing member is configured to allow passage of illumination light to the body tissue.

19. The apparatus according to claim 10, wherein said obturator sleeve has means to receive an optical imaging member for transmitting images to a proximal end of said obturator housing for viewing.

* * * * *